United States Patent

Nomura et al.

[11] Patent Number: 5,910,618
[45] Date of Patent: Jun. 8, 1999

[54] PROCESS FOR PREPARING 2,3-DIMETHYL-2-BUTENE

[75] Inventors: Kotohiro Nomura, Osaka; Michio Yamamoto, Shiga; Masashi Komatsu, Osaka, all of Japan

[73] Assignee: Sumitomo Chemical Company, Limited, Osaka, Japan

[21] Appl. No.: 08/821,572

[22] Filed: Mar. 19, 1997

Related U.S. Application Data

[63] Continuation of application No. 08/331,586, filed as application No. PCT/JP94/00346, Mar. 4, 1994, abandoned.

[51] Int. Cl.⁶ ..................................................... C07C 2/04
[52] U.S. Cl. ........................ 585/510; 585/512; 585/513; 585/664; 585/668
[58] Field of Search ..................................... 585/510, 512, 585/513, 664, 668

[56] References Cited

U.S. PATENT DOCUMENTS

| | | | |
|---|---|---|---|
| 3,173,968 | 3/1965 | Edwards et al. | 260/683.2 |
| 3,482,001 | 12/1969 | Eberhardt | 260/683.15 |
| 3,622,649 | 11/1971 | Swift et al. | 260/683.15 |
| 3,920,765 | 11/1975 | Frech et al. | 260/683.2 |
| 4,155,946 | 5/1979 | Sato et al. | 585/513 |
| 4,288,643 | 9/1981 | Weber et al. | 585/324 |
| 4,544,780 | 10/1985 | Wilson | 585/377 |
| 4,709,112 | 11/1987 | Sato et al. | 585/513 |
| 4,835,328 | 5/1989 | Kent et al. | 585/329 |
| 4,992,610 | 2/1991 | Sato et al. | 585/511 |
| 5,349,115 | 9/1994 | Nomura et al. | 585/513 |

FOREIGN PATENT DOCUMENTS

| | | |
|---|---|---|
| 2055478 | 11/1969 | Germany . |
| 2449298 | 5/1975 | Germany . |
| 71034007 | 8/1963 | Japan . |
| 72022807 | 12/1965 | Japan . |
| 48008707 | 6/1971 | Japan . |
| 54-128503 | 10/1979 | Japan . |
| 57-167932 | 10/1982 | Japan . |
| 62-158225 | 7/1987 | Japan . |
| 62-209028 | 9/1987 | Japan . |
| 63-196526 | 8/1988 | Japan . |
| 63-196527 | 8/1988 | Japan . |
| 63-280031 | 11/1988 | Japan . |
| 01221335 | 9/1989 | Japan . |
| 92147202 | 6/1992 | Japan . |
| 92270087 | 10/1992 | Japan . |
| 92346027 | 12/1992 | Japan . |

*Primary Examiner*—Shrive Beck
*Assistant Examiner*—Timothy Meeks
*Attorney, Agent, or Firm*—Birch, Stewart, Kolasch & Birch, LLP

[57] ABSTRACT

2,3-Dimethyl-2-butene is prepared by isomerizing 2,3-dimethyl-1-butene using at least one acid selected from the group consisting of sulfuric acid and sulfonic acids. By this process, 2,3-dimethyl-2-butene is effectively prepared from 2,3-dimethyl-1-butene using an inexpensive catalyst such as sulfonic acid or the sulfonic acids. Further, a dimerization reaction product of propene can also be used in the isomerization step without removing the dimerization catalyst from the reaction product.

11 Claims, No Drawings

PROCESS FOR PREPARING 2,3-DIMETHYL-2-BUTENE

This application is a continuation, of application Ser. No. 08/331,586 filed on Dec. 8, 1994, now abandoned.

FIELD OF THE INVENTION

The present invention relates to a process for preparing 2,3-dimethyl-2-butene (hereinafter referred to as "TMEN"). In particular, the present invention relates to a process for preparing TMEN by isomerizing 2,3-dimethyl-1-butene (hereinafter referred to as "DMB-1").

RELATED ART

TMEN is an important compound as a basic intermediate for agrochemicals, medicines, perfumes, cosmetic materials, and so on. For the preparation thereof, there is known a process comprising contacting DMB-1 which is synthesized by dimerization of propene with a following solid or liquid isomerization catalyst to convert DMB-1 to TMEN:

(1) A solid base catalyst such as Na—$Al_2O_3$ (cf. Japanese Patent KOKAI Publication Nos. 196526/1988, 196527/1988, 8707/1973, and the like), (2) Sulfonated divinylbenzene-styrene copolymer (cf. German Patent No. 2,449,298, Japanese Patent KOKAI Publication No. 280031/1988, and the like), (3) Molecular sieves 5A or 5-13A (cf. U.S. Pat. No. 3,636,124, German Patent No. 2,055,478, and the like), (4) $AlEt_3$/1,1,1,3,3,3-hexafluoroisopropyl alcohol catalyst (cf. Japanese Patent KOKAI Publication No. 209028/1987, and the like).

However, in a case where the above solid catalysts (1), (2) and (3) are used as the isomerization catalysts, when DMB-1 is isomerized without separating the dimerization catalyst from the dimerization reaction product, the isomerization activity and life of the catalyst are deteriorated because the solid catalyst may absorb the dimerization catalyst. Therefore, the dimerization catalyst should be removed from the dimerization reaction product.

The process which uses the liquid isomerization catalyst (4) has a drawback that an expensive alcohol is used as a catalyst component.

SUMMARY OF THE INVENTION

An object of the present invention is to provide a process for preparing TMEN from DMB-1 using the reaction product from the dimerization of propene in the isomerization process without removing the dimerization catalyst from the dimerization reaction product.

According to a first aspect of the present invention, there is provided a process for preparing TMEN comprising isomerizing DMB-1 in the presence of at least one acid selected from the group consisting of sulfuric acid and sulfonic acids.

According to a second aspect of the present invention, there is provided a process for preparing 2,3-dimethyl-2-butene comprising forming 2,3-dimethyl-1-butene from propene in the presence of a dimerization catalyst an d isomerizing formed 2,3-dimethyl-1-butene in the presence of at least one acid selected from the group consisting of sulfuric acid and sulfonic acids.

DETAILED DESCRIPTION OF THE INVENTION

The present invention will be explained in detail.

When DMB-1 is isomerized to prepare TMEN, sulfuric acid, a sulfonic acid or a mixture thereof is used as the isomerization catalyst.

Specific examples of the sulfonic acid are aliphatic sulfonic acids such as methanesulfonic acid, ethanesulfonic acid, etc.; aromatic sulfonic acids such as benzenesulfonic acid, p-toluene-sulfonic acid, etc.; halogenated sulfonic acids such as chlorosulfonic acid, etc., and mixtures thereof. It is possible to use a mixture of sulfuric acid and at least one sulfonic acid. Among sulfuric acid and the sulfonic acids, sulfuric acid and methanesulfonic acid are preferred. In particular, cheap sulfuric acid is technically advantageous.

The concentration of sulfuric acid to be used is not limited. It is usually at least 70%, preferably 90 to 98%. While an amount of sulfuric acid depends on its concentration, it is usually from 0.01 to 5.0 wt. %, preferably from 0.05 to 3.0 wt. %, more preferably from 0.05 to 1.5 wt. % based on DMB-1.

The amount of the sulfonic acid is also usually from 0.01 to 5.0 wt. %, preferably from 0.05 to 3.0 wt. %, more preferably from 0.05 to 1.5 wt. % based on DMB-1.

The isomerization reaction is usually carried out in an inactive solvent. As the inactive solvent, there are used aromatic hydrocarbons such as benzene, toluene, xylene, etc.; aliphatic hydrocarbons such as hexane, heptane, cyclohexane, etc.; halogenated hydrocarbons such as dichloromethane, dichloroethane, chloroform, chlorobenzene, dichlorobenzene, etc., and the like.

The amount of the inactive solvent is usually from 0.001 to 50 parts by weight, preferably from 0.001 to 10 parts by weight, more preferably from 0.001 to 1 part by weight per one part by weight of DMB-1.

The temperature in the isomerization reaction is usually from −30 to +100° C., preferably from 0 to 60° C.

As explained above, DMB-1 is isomerized to TMEN. TMEN can be recovered by, for example, adding an amine or an aqueous solution of an alkali to the reaction mixture after the isomerization, mixing them, separating an oil layer and distilling the oil layer.

DMB-1 which is a raw material in the process of the present invention is generally prepared by dimerizing propene using a catalyst. The dimerization catalyst is not limited insofar as DMB-1 can be formed. Specific examples of such catalyst are the following catalysts based on a nickel compound:

(1) a catalyst based on π-Allyl nickel complex/organic aluminum halide/trivalent phosphorus compound (Japanese Patent Publication No. 34007/1971, and so on), (2) a catalyst based on nickel salt/organic aluminum halide/trivalent phosphorus compound (cf. Japanese Patent Publication No. 22807/1972, and so on), (3) a catalyst based on nickel compound/trialkyl-aluminum/trivalent phosphorus compound/halogenated phenol/water (cf. Japanese Patent KOKAI Publication No. 167932/1982, and so on), (4) a catalyst based on nickel compound/trialkyl-aluminum/trivalent phosphorus compound/fluorinated isopropyl alcohol (cf. Japanese Patent KOKAI Publication Nos. 156225/1987 and 221335/1989, and so on), (5) a catalyst based on nickel compound/trialkyl-aluminum/trivalent phosphorus compound/ halogenated phenol/sulfonic acid or dialkyl sulfate (cf. Japanese Patent Application No. 346027/1992, and so on), (6) a catalyst based on nickel compound/trialkyl-aluminum/trivalent phosphorus compound/fluorinated isopropyl alcohol/sulfonic acid or dialkyl sulfate (cf. Japanese Patent Application No. 270087/1992 and so on), (7) a catalyst based on nickel compound/trialkyl-aluminum/trivalent phosphorus compound/halogenated phenol/water/sulfonic acid (cf. Japanese Patent Application No. 147202/1992, and so on).

In general, the dimerization reaction is carried out in an inactive solvent. As the inactive solvent, the same solvents as used in the above isomerization process can be exemplified.

When the dimerization catalyst described above is used, a concentration of the catalyst is usually from about $10^{-5}$ to $10^{-1}$ mol/l in terms of a concentration of nickel.

The temperature in the dimerization reaction is usually from $-70$ to $+150°$ C., preferably from $-50$ to $+100°$ C., more preferably from $-20$ to $+50°$ C. The pressure in the dimerization reaction is usually from 0 to 30 kg/cm$^2$G.

In the above manner, the dimerization reaction mixture containing DMB-1 is obtained from propene. This mixture can be supplied to the above isomerization step without removing the dimerization catalyst. Needless to say, it is possible to supply this mixture to the isomerization step after removing the catalyst by, for example, distillation and so on.

When the mixture is supplied without removing the dimerization catalyst, a yield of 2,3-dimethylbutenes (DMB-1 and TMEN) can be increased by carrying out the isomerization reaction after deactivating the dimerization catalyst by the addition of a deactivating agent such as alcohols, phenols, ammonia, amines, for example, alkylamines such as triethylamine to the dimerization reaction mixture.

The alcohol to be added is not limited. Specific examples are methanol, ethanol, n-propyl alcohol, isopropyl alcohol, n-butyl alcohol, isobutyl alcohol, tert.-butyl alcohol, and the like. Among them, isopropyl alcohol is preferably used.

As the phenols, phenol and alkyl-substituted phenols are exemplified. Examples of the alkyl-substituted phenols are o-cresol, m-cresol, p-cresol, 2,6-di-tert.-butyl-4-methylphenol (hereinafter referred to as "BHT"), and the like. Among them, BHT and p-cresol are preferably used.

The amount of the alcohol and phenol is usually from 0.01 to 10 wt. %, preferably from 0.01 to 5 wt. % based on the raw material propene.

To deactivate the dimerization catalyst, in addition to the above deactivating agent, it is possible to use an aqueous deactivating agent such as aqueous ammonia, an aqueous solution of amines, an aqueous solution of inorganic strong bases (e.g. aqueous sodium hydroxide, aqueous potassium hydroxide, etc.), an aqueous solution of mineral acids (e.g. dilute hydrochloric acid, etc.), and water. When the dimerization catalyst is deactivated by the aqueous deactivation agent, the isomerization catalyst is usually carried out after removing an aqueous layer from an oil layer containing DMB-1 and so on.

EFFECTS OF THE INVENTION

According to the present invention, TMEN can be effectively prepared from DMB-1 using an expensive catalyst such as sulfuric acid or sulfonic acids. Also, the process of the present invention is technically advantageous since the dimerization reaction mixture from propene can be used in the isomerization process even if the dimerization catalyst is not removed.

EXAMPLES

The present invention will be illustrated more in detail by the following examples, which do not limit the scope of the present invention.

Reference Example 1 (preparation of catalyst solution)

In a 50 ml Schlenk tube which had been replaced by nitrogen and cooled to 5° C., toluene (1.35 ml) containing nickel naphthenate (0.1 mmol), tricyclohexylphosphine (0.1 mmol, 20% toluene solution) and isoprene (8 mmol) were charged at the same temperature. After adding toluene (1 ml) containing triethyl-aluminum (1.0 mmol), the mixture was warmed to 18° C. while stirring.

After cooling to 5° C., trifluoromethanesulfonic acid (0.1 mmol) was added and then toluene (1.5 ml) containing 1,1,1,3,3,3-hexafluoroisopropyl alcohol (1.5 mmol) was added with maintaining an internal temperature not exceeding 20° C. to obtain a catalyst solution.

Example 1

In a 1500 ml stainless steel autoclave which had been replaced by nitrogen, the catalyst solution obtained in Reference Example 1 and toluene (40 ml) were charged at 15° C., and propene was supplied under pressure of 3 kg/cm$^2$G and reacted at 10° C. for 2 hours. After cooling the mixture to 5° C., unreacted propene was discharged outside the system.

The reaction mixture was analyzed by gas chromatography to find that a produced amount of DMB-1 was 3821 mmol, and TMEN was not detected. The selectivity of the dimers was 74.5%, and a ratio of DMB-1 in the dimers was 78.4%. T.O.N. of DMB-1 was 38210.

To the above reaction mixture, 90% sulfuric acid was added in an amount of 0.4 wt. % based on the raw material propene, and the reaction was effected at 30° C. for 3 hours. The reaction mixture was analyzed by gas chromatography, and the results are shown in Table 1.

Dimers: DMB-1, TMEN, 2M1P, 2M2P, 4M1,2P and Hex.
(DMB-1: 2,3-dimethyl-1-butene, TMEN: 2,3-dimethyl-2-butene, 2M1P: 2-methyl-1-pentene, 2M2P: 2-methyl-2-pentene, 4M1,2P: 4-methyl-1-pentene and 4-methyl-2-pentene, Hex: hexene)

Selectivity of dimers (%)=[Amount of produced dimers (g)/Amount of reacted propene (g)]×100

T.O.N. (turnover number)=Produced amount (mmol)/Nickel amount in catalyst (mmol)

Examples 2–6

Under the same conditions as in Example 1 except that a concentration and an amount of sulfuric acid were changed as shown in Table 1, the reaction was effected.

After the reaction, the resulting reaction mixture was analyzed by gas chromatography. The results are shown in Table 1.

TABLE 1

| Example No. | Sulfuric acid Concentration (%) | Sulfuric acid Amount[1] (wt. %) | TMEN ratio[2] (%) | Recovery rate[3] (%) |
|---|---|---|---|---|
| Ex. 1 | 90 | 0.4 | 91.0 | 96.2 |
| Ex. 2 | 90 | 0.35 | 89.9 | 96.1 |
| Ex. 3 | 93 | 0.1 | 89.6 | 97.0 |
| Ex. 4 | 93 | 0.2 | 90.6 | 94.9 |
| Ex. 5 | 93 | 0.3 | 91.6 | 94.2 |
| Ex. 6 | 95 | 0.2 | 88.2 | 99.3 |

[1] Amount: Weight % based on the raw material propene.
[2] TMEN ratio (%)
= Ratio of TMEN in 2,3-dimethylbutenes after the isomerization reaction.
= [Amount of TMEN (mmol) after the isomerization reaction/Amounts of 2,3-dimethylbutenes (mmol) after the isomerization reaction] × 100.
[3] Recovery rate (%)
= Recovery rate (%) of 2,3-dimethylbutenes after the isomerization reaction
= [(Amounts of 2,3-dimethylbutenes (mmol) after the isomerization reaction)/(Amounts of 2,3-dimethylbutenes (mmol) before the isomerization reaction)] × 100.

Examples 7 and 8

Under the same conditions as in the Example 1 except that the amount of sulfuric acid, and a temperature and a time of the isomerization reaction were changed as shown in Table 2, the reaction was carried out.

After the reaction, the resulting reaction mixture was analyzed by gas chromatography. The results are shown in Table 2.

TABLE 2

| Example No. | Sulfuric acid Concentration (%) | Sulfuric acid Amount (wt. %) | Isomerization reaction Temp. (° C.) | Isomerization reaction Time (hr) | TMEN ratio (%) | Recovery rate (%) |
|---|---|---|---|---|---|---|
| Ex. 7 | 90 | 0.5 | 40 | 2 | 91.5 | 93.2 |
| Ex. 8 | 90 | 0.3 | 40 | 2 | 88.1 | 94.3 |

Comparative Example 1

Under the same conditions as in Example 8 except that AMBERLIST 15 (a strongly acidic cation exchange resin manufactured by Rohm & Haas Co., U.S.A.) in an amount of 1.0 wt. % based on the raw material propene was used in place of sulfuric acid, the reaction was carried out.

After the reaction, the resulting reaction mixture was analyzed by gas chromatography. The results are shown in Table 3.

TABLE 3

| Example No. | Sulfuric acid Concentration (%) | Sulfuric acid Amount (wt. %) | Amount of AMBERLIST 15 (wt. %) | TMEN ratio (%) |
|---|---|---|---|---|
| Ex. 8 | 90 | 0.3 | — | 88.1 |
| C. Ex. 1 | — | — | 1.0 | 51.7 |

Example 9

Under the same conditions as in Example 1 except that methanesulfonic acid was used in an amount of 0.75 wt. % based on the raw material propene in place of sulfuric acid and the reaction was carried out at 40° C. for 3 hours, the reaction was effected.

After the reaction, the resulting reaction mixture was analyzed by gas chromatography. The TMEN ratio in the 2,3-dimethylbutenes after the isomerization reaction was 88.2%, and the recovery rate of the 2,3-dimethylbutenes was 99.3%.

Example 10

Under the same conditions as in Example 1, propene was dimerized. To the obtained reaction mixture, 2,6-di-tert.-butyl-4-methylphenol (BHT) was added in an amount of 0.2 wt. % based on the raw material propene at 25° C. followed by stirring for 5 minutes. To the mixture, 90% sulfuric acid was added in an amount of 0.35 wt. % based on the raw material propene and the isomerization reaction was carried out at 30° C. for 3 hours. After the reaction, the reaction mixture was analyzed by gas chromatography. The results are shown in Table 4.

Examples 11 to 15

Under the same conditions as in Example 10 except that a phenol compound of Table 4 was used in an amount shown in Table 4 instead of using 2,6-di-tert.-butyl-4-methylphenol (BHT) in an amount of 0.2 wt. % based on the raw material propene, and a concentration and an amount of sulfuric acid were changed as shown in Table 4, the reaction was effected.

After the reaction, the reaction mixture was analyzed by gas chromatography. The results are shown in Table 4.

TABLE 4

| Exam. No. | Phenol Kind | Phenol Amount[1] | Sulfuric acid Conc. | Sulfuric acid Amount[1] | TMEN ratio (%) | Recovery rate (%) |
|---|---|---|---|---|---|---|
| Ex. 10 | BHT | 0.2 | 90% | 0.35 | 92.7 | 97.2 |
| Ex. 11 | BHT | 0.2 | 90% | 0.50 | 93.2 | >99.9 |
| Ex. 12 | BHT | 0.1 | 90% | 0.50 | 91.6 | 99.6 |
| Ex. 13 | p-Cresol | 0.2 | 90% | 0.50 | 90.9 | >99.9 |
| Ex. 14 | Phenol | 0.2 | 90% | 0.50 | 90.3 | 96.8 |
| Ex. 15 | BHT | 0.2 | 93% | 0.30 | 91.0 | 98.3 |

Example 16

Under the same conditions as in Example 1, propene was dimerized. To the obtained reaction mixture, isopropyl alcohol (0.5 ml) was added at 25° C. followed by stirring for 5 minutes. To the mixture, 90% sulfuric acid was added in an amount of 0.30 wt. % based on the raw material propene and the isomerization reaction was carried out at 40° C. for 2 hours. After the reaction, the reaction mixture was analyzed by gas chromatography. The TMEN ratio in the 2,3-dimethylbutenes was 90.3%, and the recovery rate of the 2,3-dimethylbutenes was 97.4% or higher.

Example 17

In a 1500 ml stainless steel autoclave which had been replaced by nitrogen, the catalyst solution obtained in Reference Example 1 and toluene (40 ml) were charged at 15° C., and propene was supplied under pressure of 3 kg/cm$^2$G and reacted at 10° C. for 2 hours. After cooling the mixture to 5° C., unreacted propene was discharged outside the system.

To the reaction mixture, a 2% aqueous solution of sodium hydroxide was added in an amount of 50 wt. % based on the reaction liquid, followed by stirring at 40° C. for 30 minutes. After cooling it to 30° C., the mixture was kept standing and phase separated to obtain an oily layer. The oily layer was analyzed by gas chromatography to find that an amount of the dimers in the oily layer was 98% or higher of the whole dimers formed by the reaction.

One hundred grams of the obtained oily layer was charged in a 500 ml autoclave, and 95% sulfuric acid (0.7 g) was dropwise added thereto over a period of 30 minutes with keeping the temperature of the reaction mixture not exceeding 30° C. The obtained reaction mixture was analyzed by gas chromatography to find that the TMEN ratio in the 2,3-dimethylbutenes after the isomerization reaction was 92.5%, and the recovery of the 2,3-dimethylbutenes was 99%.

Examples 18 to 24

Under the same conditions as in Example 17 except that a concentration and an amount of sulfuric acid and a reaction temperature were changed as shown in Table 5, the reaction was effected. The results are shown in Table 5.

TABLE 5

| Exam. No. | Sulfuric acid Conc. (%) | Sulfuric acid Amount (g) | Reaction temp. (° C.) | TMEN ratio (%) | Recovery rate (%) |
|---|---|---|---|---|---|
| Ex. 17 | 95 | 0.7 | 30 | 92.5 | 99 |
| Ex. 18 | 93 | 0.7 | 30 | 90.9 | 99 |
| Ex. 19 | 93 | 1.0 | 30 | 91.5 | 99 |
| Ex. 20 | 93 | 1.0 | 40 | 92.0 | 99 |
| Ex. 21 | 95 | 0.5 | 30 | 93.1 | 99 |
| Ex. 22 | 95 | 0.8 | 30 | 92.9 | 99 |
| Ex. 23 | 95 | 1.0 | 30 | 92.3 | 99 |
| Ex. 24 | 97 | 0.7 | 30 | 91.7 | 99 |

Comparative Example 2

Under the same conditions as in Example 20 except that AMBERLIST 15 (1.0 g) was used in place of sulfuric acid, the reaction was carried out.

After the reaction, the reaction mixture was analyzed by gas chromatography. The results are shown in Table 6.

TABLE 6

| Exam. No. | 93% sulfuric acid (g) | AMBERLIST 15 (g) | TMEN ratio (%) |
|---|---|---|---|
| Ex. 20 | 1.0 | — | 92.0 |
| C. Ex. 2 | — | 1.0 | 46.8 |

We claim:

1. A process for preparing 2,3-dimethyl-2-butene consisting essentially of isomerizing 2,3-dimethyl-1-butene by adding at least one acid selected from the group consisting of aqueous solutions of sulfuric acid having a concentration of 90 to 98%, aliphatic sulfonic acids, aromatic sulfonic acids and halogenated sulfonic acids to 2,3-dimethyl-1-butene.

2. The process according to claim 1, wherein 2,3-dimethyl-1-butene, which is formed from propene in the presence of a dimerization catalyst, is isomerized.

3. The process according to claim 2, wherein said dimerization catalyst is deactivated after dimerization of propene to form the 2,3-dimethyl-1-butene before the 2,3-dimethyl-1-butene is isomerized.

4. The process according to claim 3, wherein said dimerization catalyst is deactivated with at least one compound selected from the group consisting of alcohols, phenols, ammonia and amines.

5. The process according to claim 2, wherein said dimerization catalyst is a homogeneous catalyst.

6. The process according to claim 5, wherein said homogeneous catalyst is at least one catalyst, which comprises a nickel compound, selected from the group consisting of (1) a catalyst based on π-allyl nickel complex/organic aluminum halide/trivalent phosphorus compound, (2) a catalyst based on nickel salt/organic aluminum halide/trivalent phosphorus compound, (3) a catalyst based on nickel compound/trialkylaluminum/trivalent phosphorus compound/halogenated phenol/water, (4) a catalyst based on nickel compound/trialkylaluminum/trivalent phosphorus compound/fluorinated isopropyl alcohol, (5) a catalyst based on nickel compound/trialkylaluminum/trivalent phosphorus compound/halogenated phenol/sulfonic acid or dialkyl sulfate, (6) a catalyst based on nickel compound/trialkylaluminum/trivalent phosphorus compound/fluorinated isopropyl alcohol/sulfonic acid or dialkyl sulfate and (7) a catalyst based on nickel compound/trialkylaluminum/trivalent phosphorus compound/halogenated phenol/water/sulfonic acid.

7. The process according to claim 1 or 2, wherein said acid is used in an amount of 0.001 to 5 wt. % based on the 2,3-dimethyl-1-butene.

8. The process according to claim 1 or 2, wherein the 2,3-dimethyl-1-butene is isomerized in the presence of at least one solvent selected from the group consisting of aromatic hydrocarbons, aliphatic hydrocarbons and halogenated hydrocarbons.

9. The process according to claim 1 or 2, wherein an amount of said solvent is from 0.01 to 50 parts by weight per one part of the 2,3-dimethyl-1-butene.

10. The process according to claim 1 or 2, wherein the 2,3-dimethyl-1-butene is isomerized at a reaction temperature from −30 to 100° C.

11. The process according to claim 1 or 2, wherein the 2,3-dimethyl-1-butene is isomerized in the presence of aliphatic, aromatic or halogenated sulfonic acids.

* * * * *

UNITED STATES PATENT AND TRADEMARK OFFICE
CERTIFICATE OF CORRECTION

PATENT NO.    : 5,910,618
DATED         : June 8, 1999
INVENTOR(S)   : Nomura et al.

It is certified that error appears in the above-identified patent and that said Letters Patent is hereby corrected as shown below:

<u>Title page,</u>
Item [30], please insert "[30] Foreign Application Priority Data" as follows:

-- [30]        Foreign Application Priority Data
March 4, 1993 [JP] Japan ……………………….. 5-043843
July 28, 1993 [JP] Japan ………………………. 5-186182
March 4, 1994 [WO] WIPO ………………….. PCT/JP94/00346 --.

Item "[22] Filed", please change "Mar. 19, 1997" to correctly read -- Mar.18, 1997 --.

Signed and Sealed this

Twentieth Day of August, 2002

Attest:

Attesting Officer

JAMES E. ROGAN
*Director of the United States Patent and Trademark Office*